(12) United States Patent
Arbore (10) Patent No.: US 10,295,838 B1
(45) Date of Patent: May 21, 2019

(54) BODY INCLUDING SURFACE HAVING CONCENTRIC ANNULAR PORTIONS

(71) Applicant: Apple Inc., Cupertino, CA (US)

(72) Inventor: Mark A. Arbore, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 15/267,321

(22) Filed: Sep. 16, 2016

Related U.S. Application Data (60) Provisional application No. 62/234,788, filed on Sep. 30, 2015.

(51) Int. Cl.
| | |
|---|---|
| *G02B 27/09* | (2006.01) |
| *G02B 27/46* | (2006.01) |
| *G01N 21/00* | (2006.01) |
| *G01N 21/47* | (2006.01) |
| *G01N 21/88* | (2006.01) |

(Continued)

(52) U.S. Cl.
CPC ......... *G02B 27/46* (2013.01); *G01N 21/4133* (2013.01); *G01N 21/49* (2013.01); *G01N 21/8806* (2013.01); *G02B 27/4233* (2013.01); *G01N 2201/0633* (2013.01)

(58) Field of Classification Search
CPC .............. G02B 5/3083; G02B 21/0016; G02B 21/0092; G02B 27/46; G02B 27/4233; G01N 21/8806; G01N 21/9501; G01N 21/4133; G01N 21/49; G01N 2201/0633; H01J 37/28; H01J 2237/024;

(Continued)

(56) References Cited

U.S. PATENT DOCUMENTS 4,634,880 A * 1/1987 Lindow .................. G01N 21/21
250/566
5,483,261 A 1/1996 Yasutake
(Continued)

FOREIGN PATENT DOCUMENTS

JP 2000-163031 A 6/2000
JP 2002-342033 A 11/2002

OTHER PUBLICATIONS

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.
(Continued)

*Primary Examiner* — Sang H Nguyen
(74) *Attorney, Agent, or Firm* — Morrison & Foerster LLP (57) ABSTRACT

A confocal inspection system can analyze light collected from a sample. For absorptive samples, it can be desirable to bin the collected light as a function of optical path length traversed in the sample. To perform this binning, the optical system can direct the collected light to a body having a surface that includes concentric annular portions that impart unique non-focusing angular redirections to respective portions of the collected light. In some examples, the annular portions are planar and have respective surface normals that are uniquely angled with respect to one another. In other examples, the annular portions are planar and parallel, and include respective zero-power, blazed diffraction gratings having unique combinations of blaze angle and blaze orientation with respect to one another. Light from each annular portion can be focused onto a respective lateral location at a detector plane.

23 Claims, 11 Drawing Sheets

(51) Int. Cl.
*G01N 21/41* (2006.01)
*G01N 21/49* (2006.01)
*G02B 27/42* (2006.01)

(58) Field of Classification Search
CPC ....... H01J 2237/0635; H01J 2237/1503; H01J 2237/20228; H01J 2237/2817
See application file for complete search history.

(56) References Cited

U.S. PATENT DOCUMENTS

| | | | |
|---|---|---|---|
| 5,488,204 | A | 1/1996 | Mead et al. |
| 5,526,338 | A * | 6/1996 | Hasman ............... G11B 7/0037 369/102 |
| 5,583,342 | A * | 12/1996 | Ichie ...................... G02B 5/001 250/458.1 |
| 5,825,352 | A | 10/1998 | Bisset et al. |
| 5,835,079 | A | 11/1998 | Shieh |
| 5,880,411 | A | 3/1999 | Gillespie et al. |
| 6,188,391 | B1 | 2/2001 | Seely et al. |
| 6,310,610 | B1 | 10/2001 | Beaton et al. |
| 6,323,846 | B1 | 11/2001 | Westerman et al. |
| 6,690,387 | B2 | 2/2004 | Zimmerman et al. |
| 7,015,894 | B2 | 3/2006 | Morohoshi |
| 7,184,064 | B2 | 2/2007 | Zimmerman et al. |
| 7,223,232 | B2 * | 5/2007 | Mizuno ............... A61B 5/0068 250/461.2 |
| 7,663,607 | B2 | 2/2010 | Hotelling et al. |
| 8,479,122 | B2 | 7/2013 | Hotelling et al. |
| 9,696,264 | B2 * | 7/2017 | Lange ................ G01N 21/9501 |
| 2005/0046818 | A1 * | 3/2005 | Neil ...................... G02B 5/001 355/55 |
| 2006/0063991 | A1 * | 3/2006 | Yu ..................... A61B 5/14532 600/322 |
| 2006/0197753 | A1 | 9/2006 | Hotelling |
| 2008/0031509 | A1 * | 2/2008 | Heiden ............. G01B 11/0608 382/145 |
| 2012/0019821 | A1 * | 1/2012 | Chen .................. G02B 21/0032 356/303 |
| 2013/0176574 | A1 * | 7/2013 | Sirat .................. G02B 21/0056 356/496 |
| 2015/0034810 | A1 * | 2/2015 | Iketaki ............... G02B 21/0032 250/225 |
| 2015/0338639 | A1 * | 11/2015 | Matsumoto ........ G02B 21/0032 359/279 |
| 2016/0025970 | A1 * | 1/2016 | Fukuyama ............. G02B 13/22 359/279 |

OTHER PUBLICATIONS

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.
Rubine, D.H. (May 1992). "Combining Gestures and Direct Manipulation," CHI '92, pp. 659-660.
Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

* cited by examiner

BODY INCLUDING SURFACE HAVING CONCENTRIC ANNULAR PORTIONS

CROSS-REFERENCE TO RELATED APPLICATION

This application claims the benefit of U.S. Provisional Application No. 62/234,788, filed Sep. 30, 2015, which is hereby incorporated by reference in its entirety herein.

TECHNICAL FIELD

The present disclosure relates to a body including a surface having concentric annular portions, and a confocal inspection system including such a body.

BACKGROUND

Many common optical inspection systems generate images of a sample. A typical inspection system can form an image in which a specified depth within the sample is sharply in focus, while depths away from the specified depths are blurred due to defocus. A confocal inspection system can attenuate, rather than blur, depths away from the specified depth, so that the confocal system can produce images of a single plane at the specified depth within the sample.

SUMMARY OF THE DISCLOSURE

A confocal inspection system can analyze light collected from a sample. For absorptive samples, it can be desirable to bin the collected light as a function of optical path length traversed in the sample. To perform this binning, the optical system can direct the collected light to a body having a surface that includes concentric annular portions that impart unique, and optionally non-focusing, angular redirections to respective portions of the collected light. In some examples, the annular portions are planar and have respective surface normals that are uniquely angled with respect to one another. In other examples, the annular portions are planar and parallel, and include respective zero-power, blazed diffraction gratings having unique combinations of blaze angle and blaze orientation with respect to one another. Light from each annular portion can be focused onto a respective lateral location at a detector plane. In some examples, one or more of the annular portions can include curvature, so that the annular portions can focus light passing through the annular portions to the detector plane, without the need for an additional focusing lens.

In some examples, a body can define a central axis and an annular surface. The annular surface can include a plurality of concentric arcuate portions surrounding the central axis. The plurality of concentric arcuate portions can have inner and outer boundaries that are at least portions of circles when viewed along the central axis. The plurality of concentric arcuate portions can be planar and can have respective surface normals that are uniquely angled with respect to one another.

In some examples, a body can define a central axis and an annular surface. The annular surface can include a plurality of concentric arcuate portions surrounding the central axis. The plurality of concentric annular portions can have inner and outer boundaries that are at least portions of circles when viewed along the central axis. The plurality of concentric arcuate portions can being planar and parallel, and can have respective zero-power, blazed diffraction gratings disposed thereon. The zero-power blazed diffraction gratings can include unique combinations of blaze angle and blaze orientation with respect to one another.

Some examples can include a confocal inspection system. A confocal assembly can be configured to collimate light reflected from a specified plane to form a collimated first beam propagating along a central axis. An annular surface can be positioned to receive the first collimated beam. The annular surface can include a plurality of concentric arcuate portions surrounding the central axis. The plurality of concentric arcuate portions can have circular inner and outer boundaries when viewed along the central axis. The plurality of concentric arcuate portions can be being planar and can have respective surface normals that are uniquely angled with respect to one another. The plurality of concentric arcuate portions can be configured to impart non-focusing angular redirections to respective portions of the first collimated beam incident thereon to produce a plurality of second collimated beams. Each of the plurality of second collimated beams can correspond to a respective concentric arcuate portion. A focusing lens can have a front focal plane coincident with the annular surface. The focusing lens can be positioned to focus the plurality of second collimated beams onto a detector plane.

Some examples can include a method for confocally inspecting a sample. Light reflected from a specified plane can be collimated to form a first collimated beam propagating along a central axis. The first collimated beam can be separated into a plurality of annular zones. The annular zones can be concentric with the central axis and can have circular inner and outer boundaries when viewed along the central axis. Unique non-focusing angular redirections can be imparted to the respective annular zones in the first collimated beam to form a plurality of second collimated beams. Each of the plurality of second collimated beams can correspond to a respective annular zone. The plurality of second collimated beams can be focused onto a detector plane. Light in each annular zone can be focused onto a respective lateral location at the detector plane.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

An optical inspection system can analyze light collected from a sample. For absorptive samples, it can be desirable to separate the collected light into bins as a function of optical path length traversed in the sample. For many geometries, such as geometries in which light converges to or emerges from a particular point beneath a top surface of a sample, optical path length within the sample can vary as a function of propagation angle within the sample (e.g., the angle formed between a propagation vector of a light ray and a surface normal from the top surface of the sample). For example, a particular inspection system can bin the collected light into three bins. A first bin can correspond to light having propagation angles in the sample between 0 degrees and 20 degrees. A second bin can correspond to light having propagation angles in the sample between 20 degrees and 30 degrees. A third bin can correspond to light having propagation angles in the sample between 30 degrees and 35 degrees. These are but examples; other numerical angular values can be used, and more or fewer than three bins can also be used. The system can direct light through an optical element having a surface that includes concentric annular portions (discussed in detail below) to determine the number of bins and the range of propagation angles in each bin. The inner and/or outer diameters of the annular portions can be selected to determine the range of propagation angles in each bin. The range of propagation angles (e.g., the largest propagation angle within a bin minus the smallest propagation angle within the bin) can be the same for all bins, can differ in two or more bins, or can be different for all bins. The system can include multiple detectors, or multiple detector elements, so that light in each bin can be detected separately from light in the other bins. Binning the light in this manner can be beneficial for analyzing one or more optical properties of the sample, such as refractive index, absorption coefficient, or a concentration level of a particular analyte.

A confocal inspection system can be particular well-suited to perform this type of binning as a function of optical path length traversed within the sample. A confocal system detects light reflected or scattered from a plane at one specified depth beneath the top surface of the sample, while attenuating light reflected or scattered from other planes at depths away from the specified depth. In the confocal geometry, illuminating light can be envisioned as a cone of light rays, converging to a particular point at a plane at the specified depth within the sample. (Alternatively, the illuminating light can be collimated, or can converge to a point at a depth other than the specified depth.) Scattered or reflected light can also be envisioned as a cone of light rays, emerging from the particular point at the plane at the specified depth within the sample. For configurations that collect and collimate the scattered or reflected light to produce a collimated beam, the optical path length traversed in the sample can vary as a function of position within the collimated beam. Using the three-bin example from above, rays near the center of the collimated beam can correspond to the first bin, rays near the edge of the collimated beam can correspond to the third bin, and rays between the center and the edge of the collimated beam can correspond to the second bin. In the discussion herein, it is assumed that light scattering from the specified depth can scatter due to a single scattering event. Alternatively, there can be instances when a light ray experiences multiple scattering events within a sample; for these instances, there can be deviations from an assumed optical path length for a given ray.

To perform this binning, the confocal inspection system can direct the collected, collimated light to a body having a surface that includes concentric annular portions that impart unique non-focusing angular redirections to respective portions of the collected light. In some examples, the annular portions are planar and have respective surface normals that are uniquely angled with respect to one another. In other examples, the annular portions are planar and parallel, and include respective zero-power, blazed diffraction gratings having unique combinations of blaze angle and blaze orientation with respect to one another. Light from each annular portion can be focused onto a respective lateral location at a detector plane, so that multiple detectors or a multi-element detector can detect light from each annular portion with its own detector or detector element.

Figure 1:
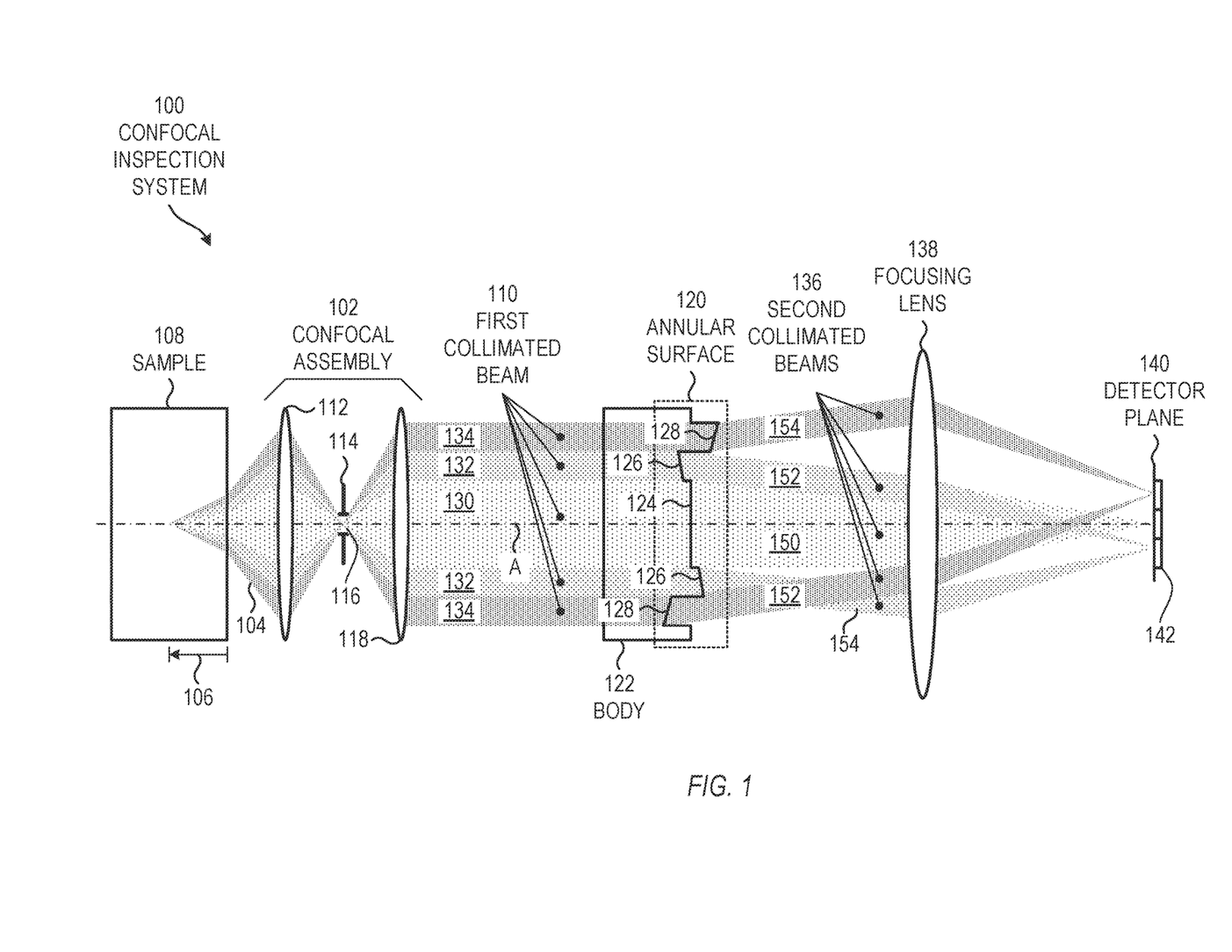
FIG. 1 shows an example of a confocal inspection system, in accordance with some embodiments.

FIG. 1 shows an example of a confocal inspection system 100, in accordance with some embodiments. The system 100 in FIG. 1 is but one example; other suitable confocal configurations can be used without departing from the scope of the present subject matter.

Confocal inspection system 100 can include an illuminator, which is omitted from FIG. 1 for clarity. The illuminator can produce light 104, and can direct the light 104 onto a surface of a sample 108 to a specified depth 106 below the surface of the sample 108. The illuminator can include a light source, which can emit light at one or more wavelengths. The illuminator can include one or more beam-steering elements, such as a mirror or beamsplitter, and one or more focusing elements, such as a lens, to direct the light 104 efficiently from the light source to the specified depth 106 below the surface of the sample 108.

FIG. 1 shows light 104 returning from to the specified depth 106 below the surface of the sample 108. Light 104 travels generally left-to-right in FIG. 1, so that a propagation vector of each light ray includes a positive (e.g., left-to-right) component parallel to a central axis (A).

In FIG. 1, light 104 is drawn as regions 130, 132, 134. In region 130, light rays have a relatively low angle of propagation within the sample 108, with respect to the central axis (A), and therefore traverse a relatively short optical path length within the sample 108. In region 132, light rays have a relatively intermediate angle of propagation within the sample 108, with respect to the central axis (A). In region 134, light rays have a relatively high angle of propagation within the sample 108, with respect to the central axis (A), and therefore traverse a relatively long optical path length within the sample 108. The confocal inspection system 100 can bin the light rays, as a function of optical path length traversed within the sample, and detect light in each bin separately from other bins. Such binning can be beneficial when analyzing samples 108 that absorb light.

A confocal assembly 102 can be configured to collimate light 104 reflected or scattered from the specified depth 106 within the sample 108 to form a collimated first beam 110 propagating along the central axis (A). The confocal assembly 102 allows light 104 from the specified depth 106 to be detected and analyzed, while rejecting light from depths away from the specified depth 106.

There are many possible configurations for the confocal assembly 102. In the example of FIG. 1, confocal assembly 102 includes a first confocal lens 112 that focuses light 104 from the sample onto a screen 114 defining an aperture 116. Light 104 that scatters or reflects from the specified depth 106 passes through the aperture 116. Light 104 that scatters or reflects from a depth away from the specified depth 106 forms a spot on the aperture 116 that is significantly larger than the aperture 116, and is therefore largely blocked by the screen 114. A second confocal lens 118 collimates the light 104 emerging from the aperture 116. This is but one example of a confocal assembly; other suitable confocal configurations can use a screen having multiple apertures, a micromirror and electronics that can selectively switch the micromirror between specified positions, an array of micromirrors and electronics that can selectively switch each micromirror between specified positions, and so forth.

An annular surface 120 can be positioned to intersect the central axis (A) and receive the first collimated beam 110. FIG. 1 shows the annular surface 120 in side-view cross-section. In the example of FIG. 1, annular surface 120 can be positioned on an incident face or an exiting face of a body 122. In some examples, annular surface 120 can be configured on an exiting surface of an optical element in the confocal assembly 102 (such as in FIG. 2). In some examples, annular surface 120 can be configured on an incident surface of a focusing lens downstream in the optical path (such as in FIG. 3).

Annular surface 120 can include a central portion 124 intersecting the central axis (A). Central portion 124 can have a circular boundary when viewed along the central axis (A). Annular surface 120 can include a plurality of concentric annular portions 126, 128 surrounding the central portion 124. The plurality of concentric annular portions 126, 128 can have circular boundaries when viewed along the central axis (A). The plurality of concentric annular portions 126, 128 can be planar and have respective surface normals that are uniquely angled with respect to one another. The central portion 124 and the plurality of concentric annular portions 126, 128 can be configured to impart non-focusing angular redirections to respective portions 130, 132, 134 of the first collimated beam 110 incident thereon to produce a plurality 136 of second collimated beams 150, 152, 154.

A focusing lens 138 can have a front focal plane coincident with the annular surface 120. Positioning the front focal plane in this manner can be referred to as being telecentric. The focusing lens 138 can be positioned to focus the plurality 136 of second collimated beams 150, 152, 154 onto a detector plane 140. Each portion 130, 132, 134 can be focused onto a respective lateral area on the detector plane 140. A multi-element detector 142 can be positioned at the detector plane 140 to detect light at each lateral area, so that light from each portion 130, 132, 134 can be detected separately from the other portions. Electronics (not shown) can record the signals from the multi-element detector 142. One or more processors (not shown) can analyze the recorded signals to determine one or more physical properties of the sample 108, such as refractive index, absorption coefficient, or a concentration level of a particular analyte.

Figure 2:
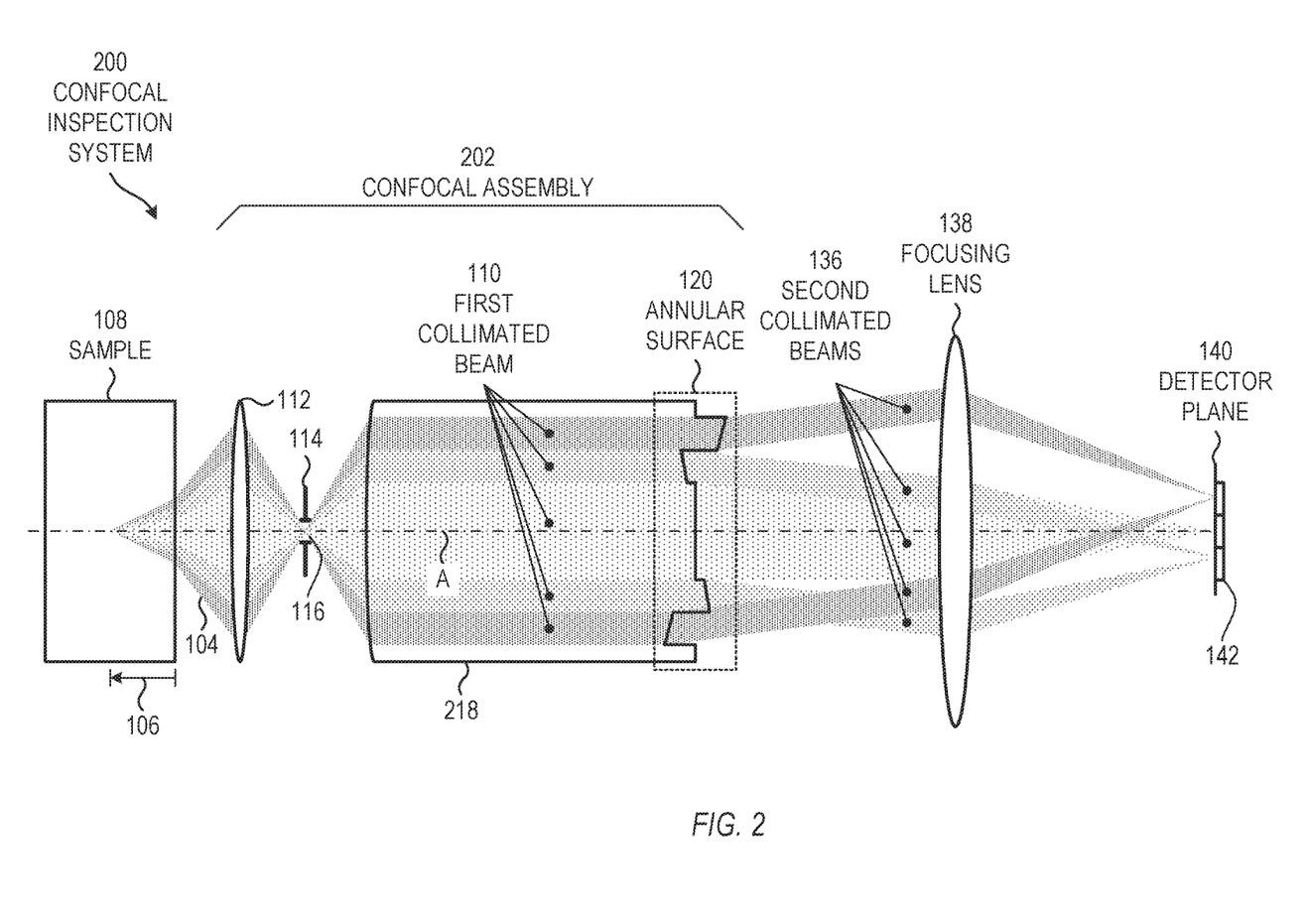
FIG. 2 shows another example of a confocal inspection system, in accordance with some embodiments.

FIG. 2 shows another example of a confocal inspection system 200, in accordance with some embodiments. In this example, the confocal inspection system 200 combines the functions of the body 122 (FIG. 1) with the confocal assembly 102 (FIG. 1). In the example of FIG. 2, annular surface 120 can be configured on an exiting surface of an optical element in the confocal assembly 202. In this example, the annular surface 120 is on the exiting surface of the second confocal lens 218.

Figure 3:
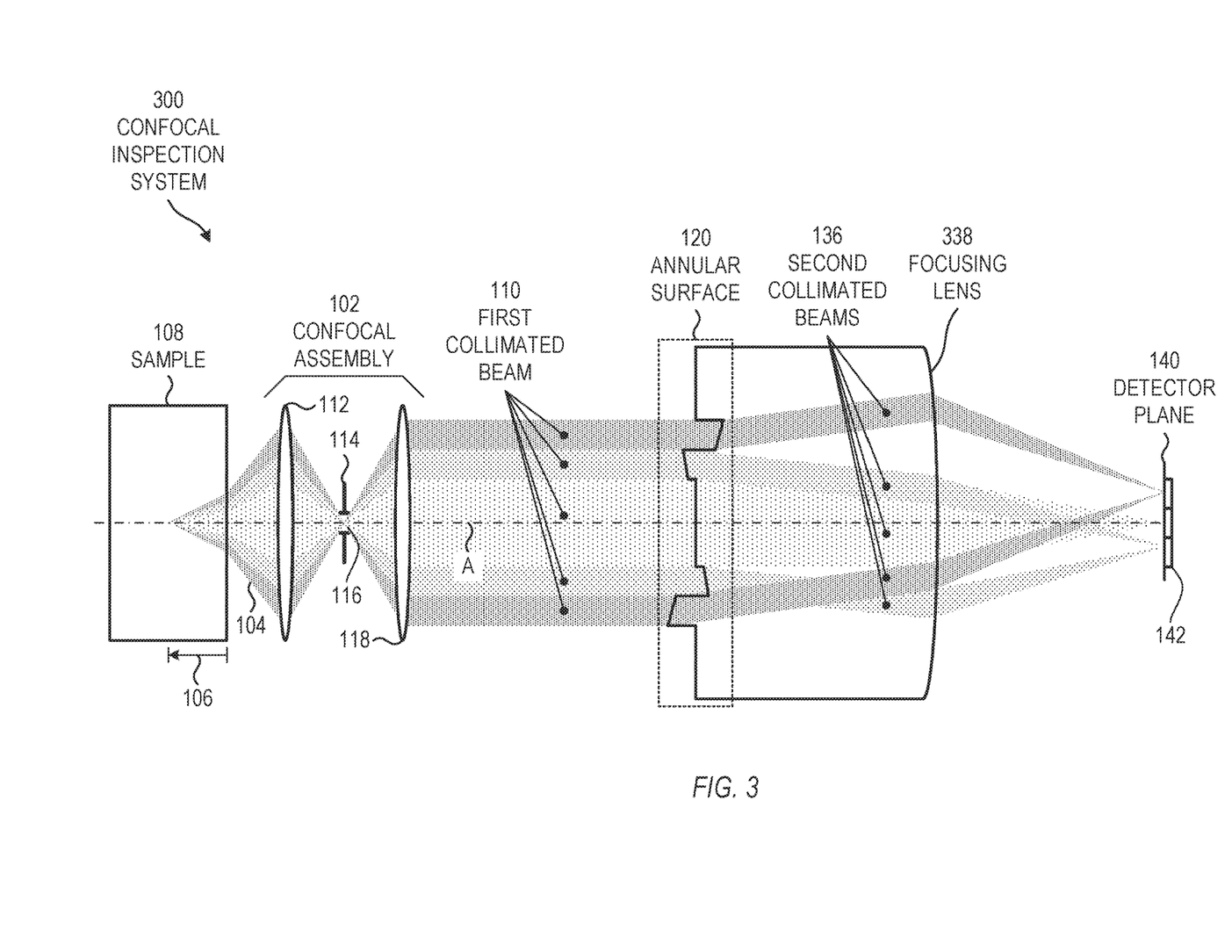
FIG. 3 shows another example of a confocal inspection system, in accordance with some embodiments.

FIG. 3 shows another example of a confocal inspection system 300, in accordance with some embodiments. In this example, the confocal inspection system 300 combines the functions of the body 122 (FIG. 1) with the focusing lens 138 (FIG. 1). In the example of FIG. 3, annular surface 120 can be configured on an incident surface of focusing lens 338.

FIGS. 1-3 are but three examples of configurations for a confocal inspection system. Other configurations can also be used.

In the examples of FIGS. 1-3, annular surface 120 includes a central portion 124 and two concentric annular portions 126, 128. In some examples, more than two concentric annular portions can be used.

Figure 4:
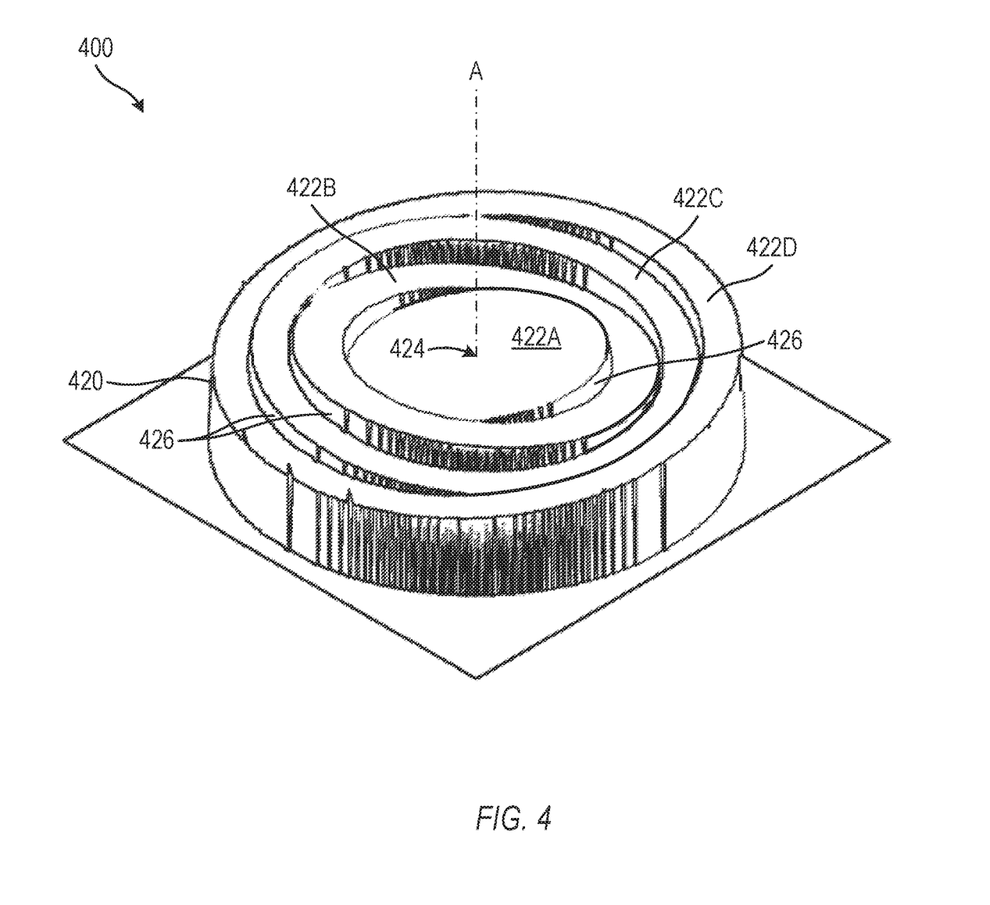
FIG. 4 shows another example of a body defining a central axis and an annular surface intersecting the central axis, in accordance with some embodiments.

FIG. 4 shows another example of a body 400 defining a central axis (A) and an annular surface 420 intersecting the central axis (A), in accordance with some embodiments. FIG. 4 shows only a portion of the body 400. Body 400 can be a stand-alone body (as in FIG. 1), an optical element in the confocal assembly (as in FIG. 2), or the focusing lens (as in FIG. 3).

Annular surface 420 includes a central portion 422A intersecting the central axis (A). Central portion 422A can have a circular boundary when viewed along the central axis (A). Annular surface 420 can include a plurality of concentric annular portions 422B-D surrounding the central portion 422A. The plurality of concentric annular portions 422B-D can have circular boundaries when viewed along the central axis (A). The plurality of concentric annular portions 422B-D can be planar and have respective surface normals that are uniquely angled with respect to one another. The central portion 422A and the plurality of concentric annular portions 422B-D can be configured to impart non-focusing angular redirections to respective portions of the first collimated beam 110 (FIG. 1) incident thereon to produce a plurality 136 of second collimated beams (FIG. 1).

In some examples, all or a portion of the body 400 can be optically transparent. Examples of optically transparent materials include, but are not limited to, an optical glass, such as N-BK57 or N-SF5, fused silica, Sapphire, ZnSe, Silicon, Germanium, a transparent plastic material, and others. In some examples, the body 400 can be optically transparent at one or more wavelengths emitted by a light source in a confocal inspection system. In some examples, at least one annular portion, of the plurality of annular portions 422B-D, can include an anti-reflection coating disposed thereon. In some examples, wherein the body 400 further includes a lens surface intersecting the central axis (A) and opposing the annular surface 420. For instance, such a lens surface can include a second confocal lens (as in FIG. 2) or a focusing lens (as in FIG. 3).

The examples in FIG. 3 show the annular surface 120 operating in transmission, so that the first collimated beam 110 and the plurality 136 of second collimated beams are on opposite sides of the annular surface 120. As an alternative, the annular surface 120 can operate in reflection, so that the first collimated beam 110 and the plurality 136 of second collimated beams are positioned on the same side of the annular surface 120. For this reflective configuration, at least one annular portion, of the plurality of annular portions, can include a high-reflection coating disposed thereon.

Each annular portion, of the plurality of annular portions 422B-D, includes a geometric center. In some examples, the geometric centers of at least two of the annular portions 422B-D coincide at a common longitudinal location along the central axis (A). In the example of FIG. 4, the geometric centers of annular portions 422B-D, as well as central portion 422A, all coincide at longitudinal location 424 along the central axis (A). This can reduce losses due to shadowing, where light from one annular portion becomes blocked by a cylindrical wall 426 at an interface between adjacent annular portions. In some examples, the annular surface 420 can include a respective wall 426 along an inner boundary of each annular portion 422B-D, each wall 426 being cylindrical and concentric with the central axis (A), each wall 426 being masked to reduce optical reflections therefrom.

In some examples, at least one annular portion, of the plurality of annular portions 422B-D, can have a planar base curvature and include a diffraction grating disposed thereon. In some examples, the grating can be a zero-power, blazed diffraction grating, which can efficiently impart a non-focusing angular redirection to a transmitted or reflected beam. Such a grating can be used in addition to, or instead of, the angling of a respective annular portion with respect to the other annular portions. For instance, the annular portions can include a combination of one or more differently-angled surface normals and one or more gratings.

In some examples, the central portion 422A is planar and has a surface normal that is uniquely angled with respect to the surface normals of the plurality of concentric annular portions 422B-D. In other examples, the central portion 422A has a planar base curvature and includes a zero-power, blazed diffraction grating disposed thereon. In still other examples, the central portion comprises an aperture concentric with the central axis (A) and extending through the body 400. For instance, a body that includes the annular surface 420 may be annular in shape, with a cylindrical passageway at its center, concentric with the central axis (A); an opening of such a cylindrical passageway can be considered to comprise the central portion 422A. In still other examples, the central portion can be masked, so that light striking the central portion is blocked from reaching a detector plane.

Figure 5:
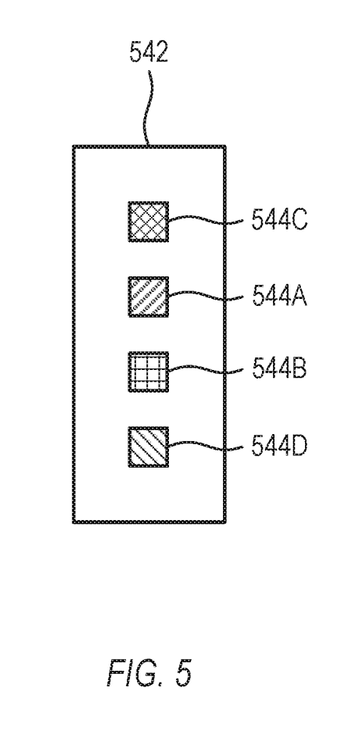
FIG. 5 shows an example of a detector, with detector elements arranged in a line, in accordance with some embodiments.

In some examples, the surface normals of the central portion 422A and the plurality of concentric annular portions 422B-D are all angled within a single plane. In other words, the non-focusing angular redirections reside in the same plane. For these examples, confining the angling to a single plane can allow a multi-element detector to be configured as a line of detector elements. FIG. 5 shows an example of a detector 542, with detector elements 544A-D arranged in a line, in accordance with some embodiments. In some examples, such as the example shown in FIG. 5, the detector elements 544A-D can be spaced apart. In other examples, the detector elements 544A-D can be spaced as close together as is practical.

Figure 6:
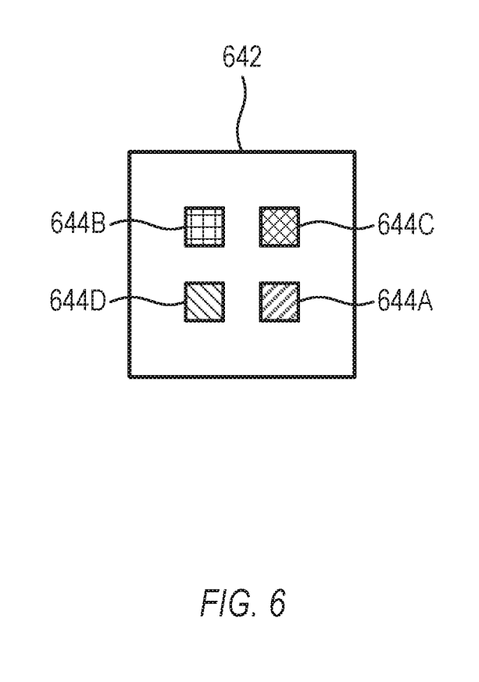
FIG. 6 shows another example of a detector, with detector elements arranged in a rectangular or square pattern, in accordance with some embodiments.

In some examples, such as the example shown in FIG. 4, the surface normals of the central portion 422A and the plurality of concentric annular portions 422B-D do not all reside within a single plane. In other words, the non-focusing angular redirections do not reside in the same plane. For these examples, allowing the angling to depart from a single plane can allow a multi-element detector to be configured as an array of detector elements. FIG. 6 shows another example of a detector 642, with detector elements 644A-D arranged in a rectangular or square pattern, in accordance with some embodiments. In some examples, such as the example shown in FIG. 6, the detector elements 644A-D can be spaced apart. In other examples, the detector elements 644A-D can be spaced as close together as is practical. In some of these examples, the detector elements 644A-D can be configured as a multi-element detector array, with detector elements positioned in a rectangular or square grid.

Figure 7:
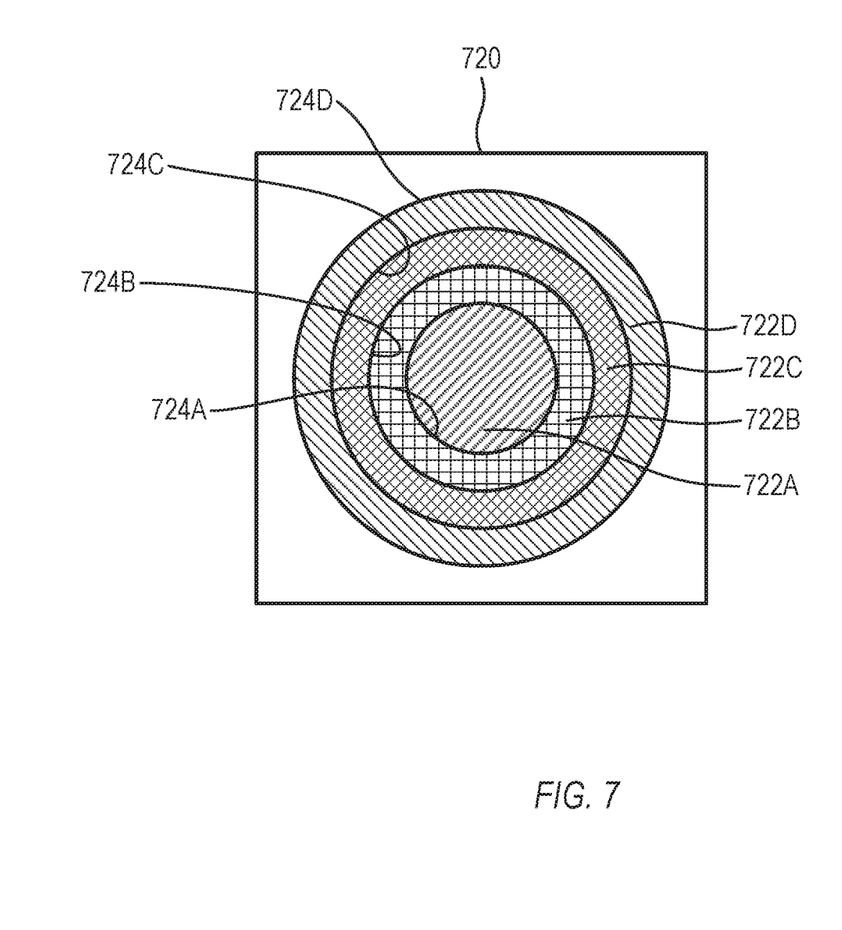
FIG. 7 shows an example of an annular surface as viewed along the central axis, in accordance with some embodiments.

FIG. 7 shows an example of an annular surface 720 as viewed along the central axis, in accordance with some embodiments. In some examples, annular surface 720 can be a subset of an overall cross-sectional shape of a body that includes the annular surface. For instance, the annular surface 720 may be circular, and may be disposed on a body having a square cross-section. Other geometries can also be used.

Annular surface 720 can include a central portion 722A intersecting the central axis and having a circular boundary 724A when viewed along the central axis. Annular surface 720 can include a plurality of concentric annular portions 722B-D surrounding the central portion 722A. The plurality of concentric annular portions 722B-D can have circular boundaries 724B-D when viewed along the central axis. In some examples, the plurality of concentric annular portions 722B-D can be planar and can have respective surface normals that are uniquely angled with respect to one another.

Figure 8:
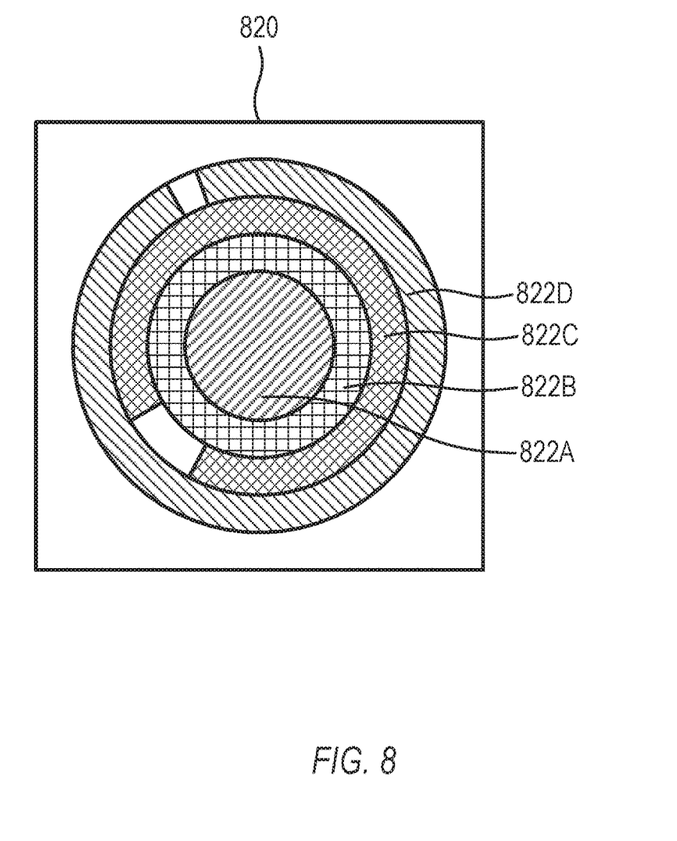
FIG. 8 shows an example of an annular surface as viewed along the central axis, in accordance with some embodiments, in which one or more of the annular portions are incomplete annuli.

In the example of FIG. 7, each of the plurality of concentric annular portions 722B-D comprises a full annulus. In other examples, one or more of the annular portions 722 B-D can be incomplete annuli. FIG. 8 shows an example of an annular surface 820 as viewed along the central axis, in accordance with some embodiments, in which one or more of the annular portions 822 B-D are incomplete annuli. For instance, annular portions 822C and 822D can be incomplete annuli. As an alternative, one or more of the incomplete annuli can include multiple non-contiguous portions. For these cases, both incomplete annular portions and complete annular portions can be referred to more generally as arcuate portions.

As an alternative to the geometries discussed above, the annular surface can have a planar base curvature (e.g., no angled portions), and can use zero-power blazed diffraction gratings to impart the non-focusing angular redirections. Such an annular surface would appear as in FIG. 7 or 8, in an end-on view, but would appear flat in a side view, and would lack the stepped or angled features shown in FIGS. 1-4.

For this alternative, a body can define a central axis and an annular surface intersecting the central axis. The annular surface can include a central portion intersecting the central axis and having a circular boundary when viewed along the central axis. The annular surface can further include a plurality of concentric annular portions surrounding the central portion. The plurality of concentric annular portions can have circular boundaries when viewed along the central axis. The plurality of concentric annular portions can be planar and parallel, and have respective zero-power, blazed diffraction gratings disposed thereon. The zero-power blazed diffraction gratings can include unique combinations of blaze angle and blaze orientation with respect to one another.

In some of these examples, each of the plurality of concentric annular portions comprises a full annulus. In other examples, at least one of the concentric annular portions includes a partial annulus, which can optionally include one or more non-contiguous portions of an annulus.

In some of these examples, at least a portion of the body is optically transparent, and the body further includes a lens surface intersecting the central axis and opposing the annular surface. In other of these examples, the body can be optically opaque, and the annular surface can operate in reflection.

In some of these examples, the blaze orientations of the zero-power blazed diffraction gratings are all the same for the plurality of concentric annular portions, and the blaze angles of the zero-power blazed diffraction gratings are all different for the plurality of concentric annular portions. These orientations can be used with multiple detector elements arranged in a line, as in FIG. 5.

In some of these examples, the central portion comprises an aperture concentric with the central axis and extending through the body.

In some of these examples, the plurality of concentric annular portions are all coplanar. In other examples, there can be height differences among two or more of the annular portions. For instance, one annular portion can extend farther along the central axis (A) than another annular portion.

Figure 9:
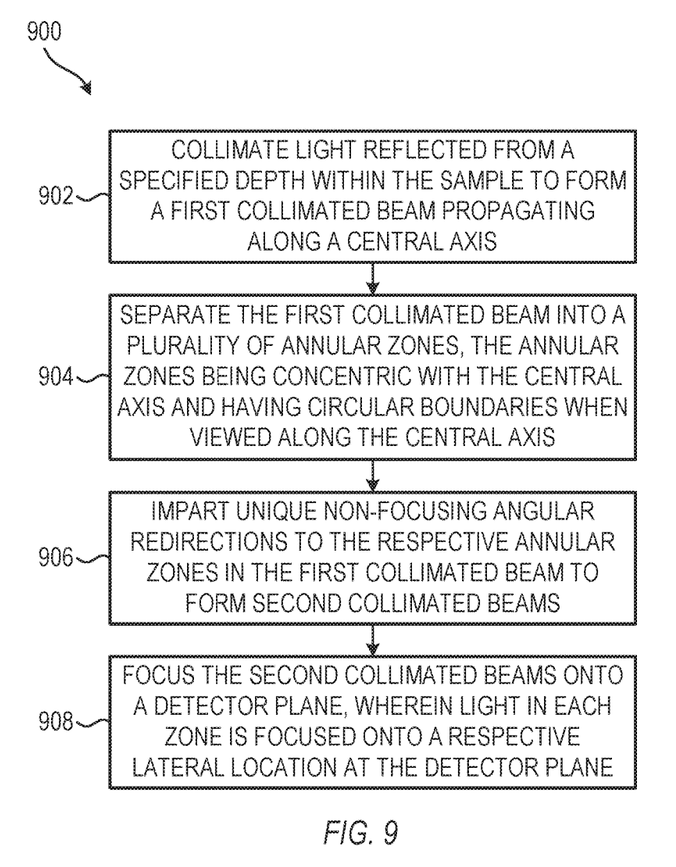
FIG. 9 shows an example of a method for confocally inspecting a sample, in accordance with some examples.

FIG. 9 shows an example of a method 900 for confocally inspecting a sample, in accordance with some examples. The method 900 can be executed on a confocal inspection system, such as 100 (FIG. 1), 200 (FIG. 2), 300 (FIG. 3), or other suitable systems. Method 900 is but one example of a method for confocally inspecting a sample; other suitable methods for confocally inspecting a sample can also be used.

At operation 902, confocal inspection system collimates light reflected from a specified depth within the sample to form a first collimated beam propagating along a central axis.

At operation 904, confocal inspection system separates the first collimated beam into a plurality of annular zones. The annular zones are concentric with the central axis and have circular boundaries when viewed along the central axis.

At operation 906, confocal inspection system imparts unique non-focusing angular redirections to the respective annular zones in the first collimated beam to form a plurality of second collimated beams. Each of the plurality of second collimated beams can correspond to a respective annular zone. In some examples, the unique non-focusing angular redirections all reside in the same plane. In other examples, the unique non-focusing angular redirections do not all reside within a single plane.

At operation 908, confocal inspection system focuses the second collimated beams onto a detector plane. Light in each zone is focused onto a respective lateral location at the detector plane. In some examples, the second collimated beams are focused telecentrically onto the detector plane.

In the examples of FIGS. 1-9, the annular surface includes concentric zones that impart redirections to beams, but do not focus the redirected beams. In other words, a collimated beam strikes the annular surface, and multiple collimated beams exit the annular surface. In the examples of confocal inspection systems shown in FIGS. 1-3, a focusing lens, or focusing lens surface away from the annular surface, focuses the light from the annular surface onto the detector plane.

Alternatively, there can be configurations in which the focusing function is integrated into the annular surface. For these configurations, a collimated beam strikes the annular surface, and multiple converging beams exit the annular surface to come to focus at the detector plane. In some examples, such a configuration can be desirable, in that it can reduce a number of optical elements in the system while maintaining the same functionality.

Figure 10:
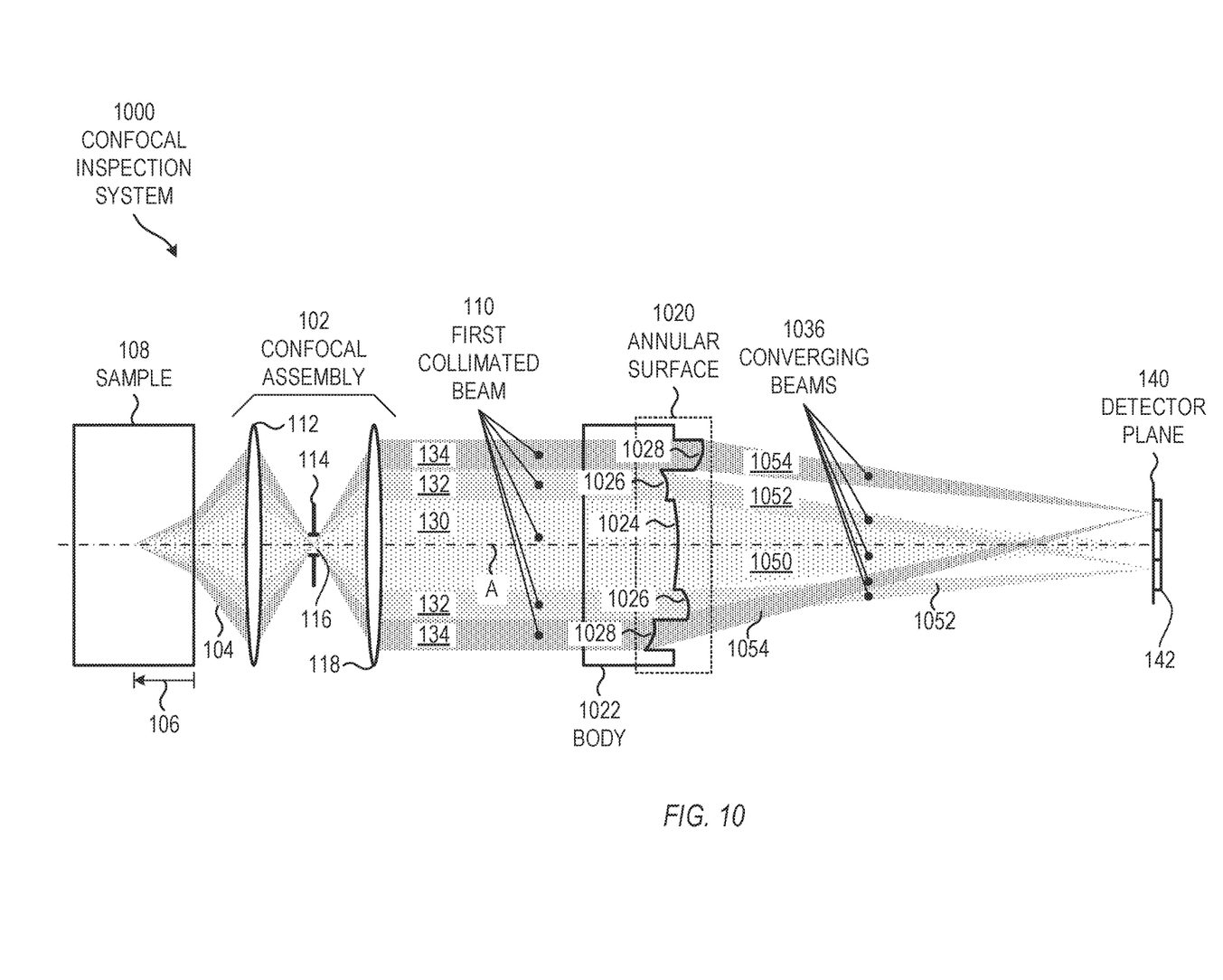
FIG. 10 shows another example of a confocal inspection system, in accordance with some embodiments.

FIG. 10 shows an example of a confocal inspection system 1000, in which the annular surface includes curvature that can focus incident light onto the detector plane 140, in accordance with some embodiments. In this example, body 1022 includes an annular surface 1020 having a central portion 1024 intersecting the central axis (A). Central portion 124 can have a circular boundary when viewed along the central axis (A). In other examples, annular surface 1020 can include a cylindrical aperture extending longitudinally through the body 1022. Annular surface 1020 can include a plurality of concentric annular portions 1026, 1028 surrounding the central portion 1024 or the cylindrical aperture. The plurality of concentric annular portions 1026, 1028 can have circular boundaries when viewed along the central axis (A).

In addition to unique angling, the plurality of concentric annular portions 1026, 1028 can include additional curvature that can focus light transmitted though (or reflected from) the annular portions 1026, 1028. Although one cannot define a unique surface normal from a curved surface, one can define a zonal axis for each annular portion 1026, 1028, where each zonal axis is defined as a longitudinal center of rotation for the surface curvature in each annular portion 1026, 1028. Each zonal axis would coincide with a corresponding surface normal, for vanishingly small surface curvatures.

The central portion 1024 and the plurality of concentric annular portions 1026, 1028 can be configured to impart focusing angular redirections to respective portions 130, 132, 134 of the first collimated beam 110 incident thereon to produce a plurality 1036 of converging beams 1050, 1052, 1054 that are focused onto respective lateral areas on the detector plane 140. The multi-element detector 142 can be positioned at the detector plane 140 to detect light at each lateral area, so that light from each portion 1030, 1032, 1034 can be detected separately from the other portions. Electronics (not shown) can record the signals from the multi-element detector 142. One or more processors (not shown) can analyze the recorded signals to determine one or more physical properties of the sample 108, such as refractive index, absorption coefficient, or a concentration level of a particular analyte.

Annular surface 1020 is not configured as a Fresnel lens, and differs from a Fresnel lens in two ways. First, each concentric annular portion 1026, 1028 focuses light to its own respective lateral area on the detector plane 140, so that respective elements of a multi-element detector 142 can sense light from a respective annular portion 1026, 1028. In contrast, the annular regions of a Fresnel lens all focus light onto a single lateral area along a central axis of the Fresnel lens. Second, the inner and outer radii of the annular portions can be selected to capture specific ranges of propagation angles of light rays within the sample. In contrast, the radii of the annular regions of a Fresnel lens are determined to produce a specific difference in on-axis optical path difference from region-to-region. Such radii for a Fresnel lens typically vary such that the outer annular regions are more closely spaced than the inner annular regions.

Figure 11:
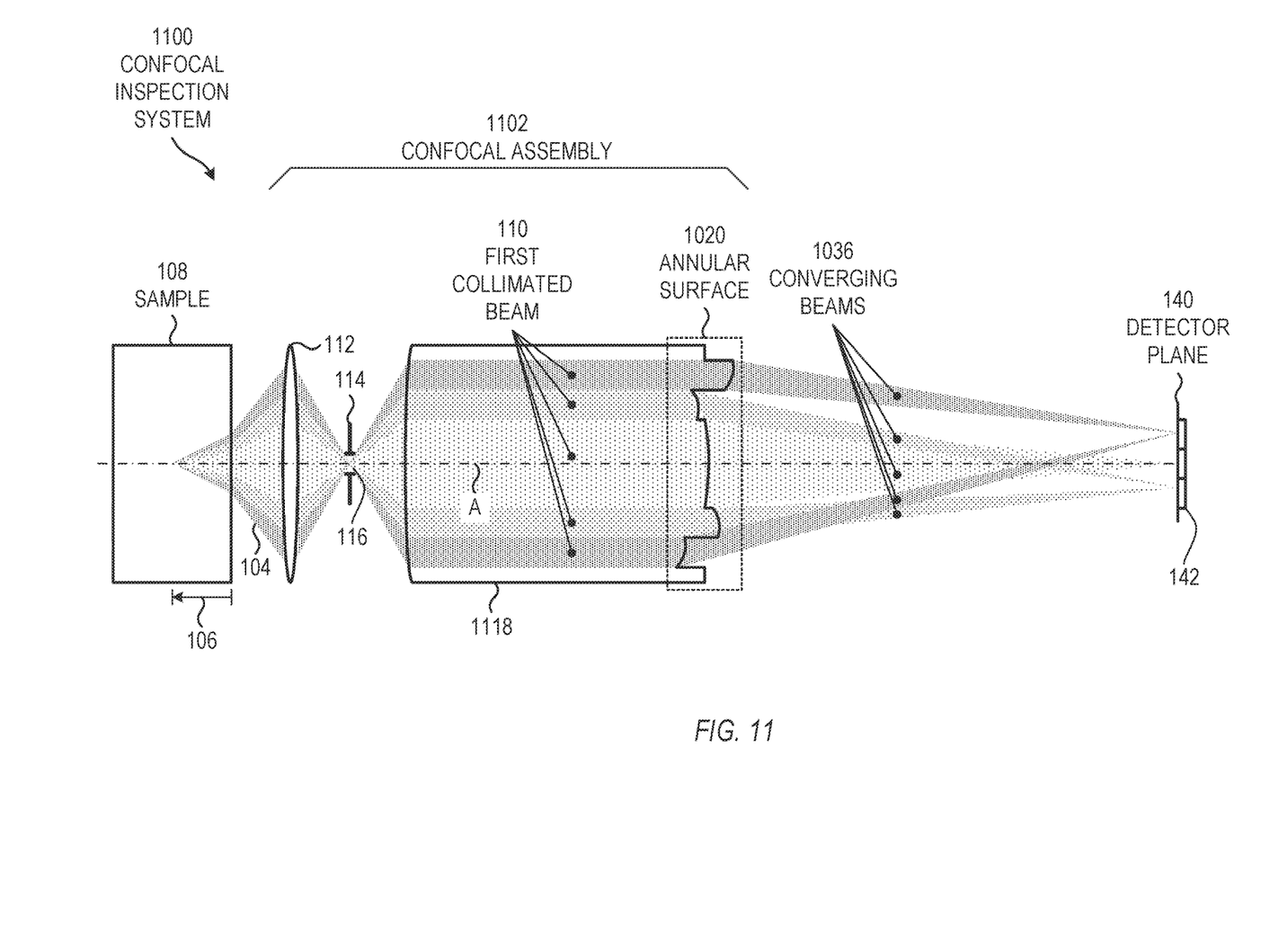
FIG. 11 shows another example of a confocal inspection system, in accordance with some embodiments.

FIG. 11 shows another example of a confocal inspection system 1100, in accordance with some embodiments. In this example, the confocal inspection system 1100 combines the functions of the body 1022 (FIG. 10) with the confocal assembly 102 (FIG. 10). In the example of FIG. 1, annular surface 1020 can be configured on an exiting surface of an optical element in the confocal assembly 1102. In this example, the annular surface 1020 is on the exiting surface of the second confocal lens 1118.

Figure 12:
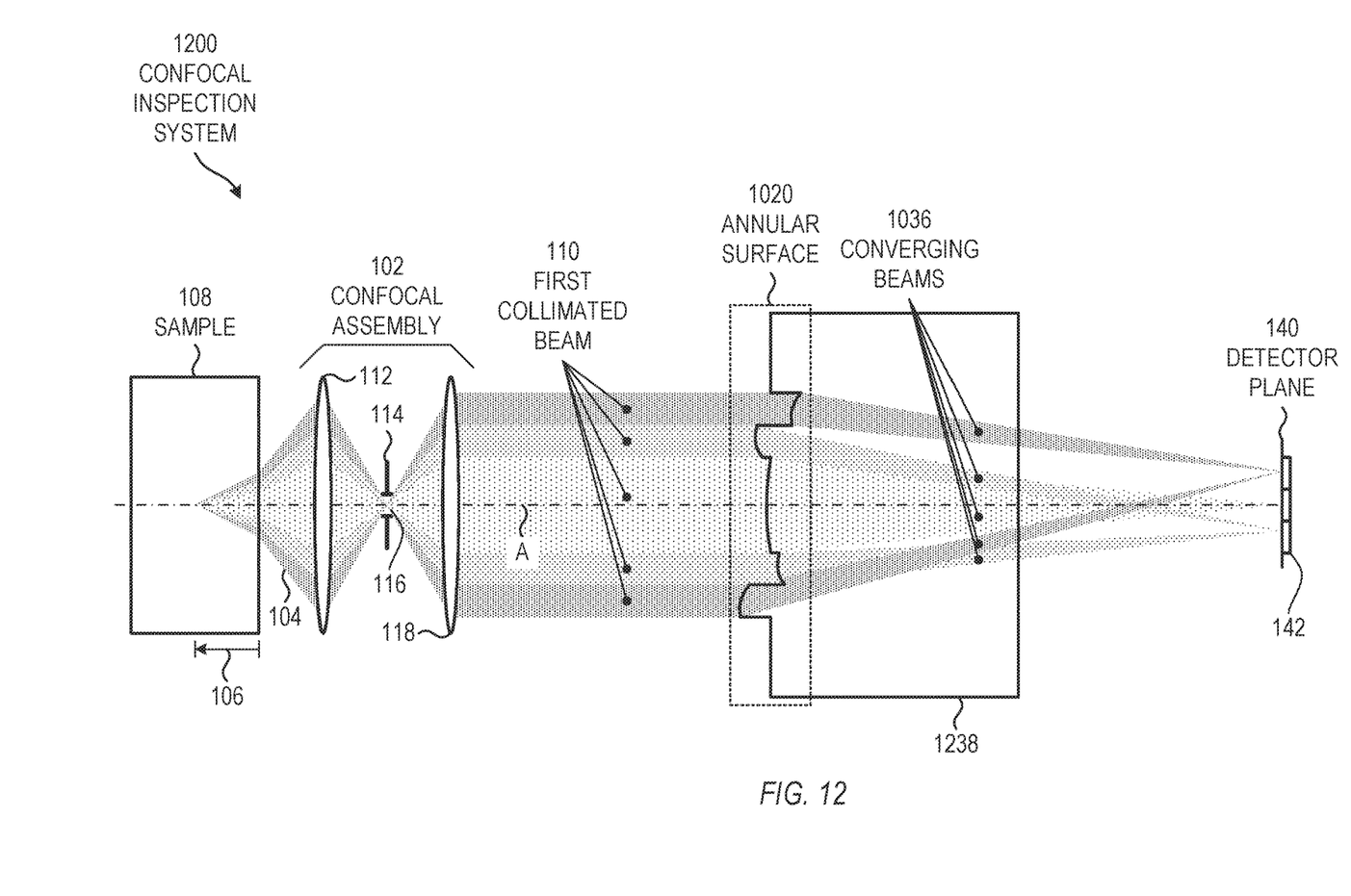
FIG. 12 shows another example of a confocal inspection system, in accordance with some embodiments.

FIG. 12 shows another example of a confocal inspection system, in accordance with some embodiments. In this example, the confocal inspection system 1200 locates the annular surface 1020 on an incident face of body 1238, in contrast with the example of FIG. 10, in which the annular surface 1020 is on an exiting face 1022. In some examples, in which the annular surface 1020 operates in reflection, rather than transmission, the concavity is reversed from the examples shown in FIGS. 10-12.

FIGS. 10-12 are but three examples of configurations for a confocal inspection system, in which the annular surface defines a plurality of arcuate (e.g., partial annular) or complete annular portions that have surface curvature that can focus light transmitted through (or reflected from) the annular portions. Other configurations can also be used.

A confocal inspection system can include processing hardware including, but not limited to, a computer. Such a computer can control one or more light sources, can optionally control a position or orientation of a sample, can process signals from detectors, can perform analysis of the signals to determine one or more properties of a sample, can store calculated results, and can optionally display results to a user on a graphical user interface. Some embodiments may be implemented in one or a combination of hardware, firmware and software. Embodiments may also be implemented as instructions stored on a computer-readable storage device, which may be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media. In some embodiments, a system or device may include one or more processors and may be configured with instructions stored on a computer-readable storage device.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A confocal inspection system, comprising:
   an illuminator that produces light;
   a confocal assembly that collimates light reflected from a specified plane to form a collimated first beam propagating along a central axis;
   an annular surface positioned to receive the first collimated beam, the annular surface including a plurality of concentric arcuate portions;
   wherein the plurality of concentric arcuate portions impart non-focusing angular redirections to respective portions of the first collimated beam incident thereon to produce a plurality of second collimated beams, each of the plurality of second collimated beams corresponding to a respective concentric arcuate portion; and
   a focusing lens having a front focal plane coincident with the annular surface, the focusing lens positioned to focus the plurality of second collimated beams onto a detector plane.

2. The confocal inspection system of claim 1, wherein the plurality of concentric arcuate portions surround the central axis, the plurality of concentric arcuate portions having inner and outer boundaries that are at least portions of circles when viewed along the central axis, the plurality of concentric arcuate portions being planar and having respective surface normals that are uniquely angled with respect to one another, and
   further wherein the annular surface is included in a body defining the central axis and annular surface.

3. The confocal inspection system of claim 2, wherein each of the plurality of concentric arcuate portions comprises a full annulus, so that the plurality of concentric arcuate portions comprises a corresponding plurality of concentric annular portions.

4. The confocal inspection system of claim 3, wherein at least a portion of the body is optically transparent.

5. The confocal inspection system of claim 4, wherein at least one annular portion, of the plurality of annular portions, includes an anti-reflection coating disposed thereon.

6. The confocal inspection system of claim 4, wherein the body further includes a lens surface intersecting the central axis and opposing the annular surface.

7. The confocal inspection system of claim 3, wherein at least one annular portion, of the plurality of annular portions, includes a high-reflection coating disposed thereon.

8. The confocal inspection system of claim 3, wherein at least one annular portion, of the plurality of annular portions, has a planar base curvature and includes a diffraction grating disposed thereon.

9. The confocal inspection system of claim 3, wherein the annular surface further comprises a central portion intersecting the central axis and positioned at a center of the plurality of concentric arcuate portions.

10. The confocal inspection system of claim 9, wherein the central portion is planar and has a surface normal that is uniquely angled with respect to the surface normals of the plurality of concentric annular portions.

11. The confocal inspection system of claim 10, wherein the surface normals of the central portion and the plurality of concentric annular portions are all angled within a single plane.

12. The confocal inspection system of claim 10, wherein the surface normals of the central portion and the plurality of concentric annular portions do not all reside within a single plane.

13. The confocal inspection system of claim 10, wherein the central portion has a planar base curvature and includes a zero-power, blazed diffraction grating disposed thereon.

14. The confocal inspection system of claim 3, wherein:
   each annular portion, of the plurality of annular portions, includes a geometric center; and
   the geometric centers of at least two of the annular portions coincide at a common longitudinal location along the central axis.

15. The confocal inspection system of claim 3, wherein the annular surface includes a respective wall along an inner boundary of each annular portion, each wall being cylindrical and concentric with the central axis, each wall being masked to reduce optical reflections therefrom.

16. The confocal inspection system of claim 3, wherein the annular surface is configured on an exiting surface of an optical element in the confocal assembly.

17. The confocal inspection system of claim 3, wherein the annular surface is configured on an incident surface of the focusing lens.

18. The confocal inspection system of claim 3, wherein the non-focusing angular redirections reside in the same plane.

19. The confocal inspection system of claim 1, wherein the non-focusing angular redirections do not reside in the same plane.

20. A method for confocally inspecting a sample, comprising:

produce light using an illuminator;

collimating light reflected from a specified plane to form a first collimated beam propagating along a central axis;

separating the first collimated beam into a plurality of annular zones, the annular zones being concentric with the central axis and having circular inner and outer boundaries when viewed along the central axis;

imparting unique non-focusing angular redirections to the respective annular zones in the first collimated beam to form a plurality of second collimated beams, each of the plurality of second collimated beams corresponding to a respective annular zone; and focusing the plurality of second collimated beams onto a detector plane, wherein light in each annular zone is focused onto a respective lateral location at the detector plane.

21. The method of claim 20, wherein the second collimated beams are focused telecentrically onto the detector plane.

22. The method of claim 20, wherein the unique non-focusing angular redirections all reside in the same plane.

23. The method of claim 20, wherein the unique non-focusing angular redirections do not all reside within a single plane.

* * * * *